United States Patent
Garel

(10) Patent No.: US 11,208,370 B2
(45) Date of Patent: Dec. 28, 2021

(54) COMPOSITIONS COMPRISING HYDROQUINONE AND CATECHOL, METHOD FOR PREPARING THESE COMPOSITIONS

(71) Applicant: RHODIA OPERATIONS, Paris (FR)

(72) Inventor: Laurent Garel, Lyons (FR)

(73) Assignee: RHODIA OPERATIONS, Aubervilliers (FR)

(*) Notice: Subject to any disclaimer, the term of this patent is extended or adjusted under 35 U.S.C. 154(b) by 0 days.

(21) Appl. No.: 16/619,878

(22) PCT Filed: Jun. 12, 2018

(86) PCT No.: PCT/EP2018/065463
§ 371 (c)(1),
(2) Date: Dec. 5, 2019

(87) PCT Pub. No.: WO2018/229033
PCT Pub. Date: Dec. 20, 2018

(65) Prior Publication Data
US 2020/0102259 A1  Apr. 2, 2020

(30) Foreign Application Priority Data
Jun. 13, 2017 (FR) ..................... 1755272

(51) Int. Cl.
*C07C 39/06* (2006.01)
*C07C 39/08* (2006.01)
*C07C 43/205* (2006.01)
*C07C 15/085* (2006.01)
*C07C 37/60* (2006.01)

(52) U.S. Cl.
CPC ............ *C07C 39/06* (2013.01); *C07C 15/085* (2013.01); *C07C 37/60* (2013.01); *C07C 39/08* (2013.01); *C07C 43/205* (2013.01); *C07C 2529/89* (2013.01)

(58) Field of Classification Search
CPC ....... C07C 39/06; C07C 15/085; C07C 37/60; C07C 39/08; C07C 43/205
See application file for complete search history.

(56) References Cited

U.S. PATENT DOCUMENTS 5,426,244 A * 6/1995 Sugai ...................... C07C 37/60
568/741

FOREIGN PATENT DOCUMENTS

WO     9802500 A1    1/1998
WO     WO-9802500 A1 * 1/1998  ............... C07C 7/20

OTHER PUBLICATIONS

"Thangaraj etal, Indian Journal of Chemistry, vol. 33A, Mar. 1994, pp. 255-258".

* cited by examiner

*Primary Examiner* — Yong L Chu
(74) *Attorney, Agent, or Firm* — Osha Bergman Watanabe & Burton LLP

(57) ABSTRACT

The present invention describes compositions comprising at least one compound chosen from hydroquinone and catechol, characterised in that it further comprises between 0.1 and 10,000 ppm of at least one compound chosen from 2-(alkoxy)phenol, 4-(alkoxy)phenol, 2-(alkyl)phenol, 4-(alkyl)phenol, (alkyl)catechol and (alkyl)hydroquinone. Another aspect of this invention concerns a method for preparing a composition comprising at least one compound chosen from hydroquinone and catechol according to the invention, characterised in that it comprises a step (a) of reacting the phenol with hydrogen peroxide in the presence of a catalyst, in a solvent comprising an alcohol.

13 Claims, No Drawings

COMPOSITIONS COMPRISING HYDROQUINONE AND CATECHOL, METHOD FOR PREPARING THESE COMPOSITIONS

CROSS-REFERENCE TO RELATED APPLICATIONS

The present application is a U.S. national stage entry under 35 U.S.C. § 371 of International Application No. PCT/EP2018/065463, filed Jun. 12, 2018, which claims priority to French Patent No. 1755272 filed Jun. 13, 2017, the entire content of these applications being incorporated herein by reference for all purposes.

TECHNICAL FIELD

The present invention relates to compositions comprising hydroquinone and/or catechol and to a process for the preparation of these compositions by hydroxylation of phenol.

PRIOR ART

Aromatic hydroxylated compounds are important compounds in organic synthesis. Different routes for the synthesis of these products have been developed over time, in particular by hydroxylation of phenol in the presence of a catalyst. The reaction for the hydroxylation of phenol results in two isomers being obtained, namely 1,4-dihydroxybenzene or hydroquinone (HQ) and 1,2-dihydroxybenzene or catechol (PC), which are compounds having a high industrial potential. Hydroquinone is a product used in numerous fields of application as polymerization inhibitor, antioxidant in elastomers or as synthetic intermediate. Another field of application is photography. For its part, catechol is a widely used product, in particular used as intermediate in the synthesis of molecules which may be used in varied applications, such as pharmaceuticals, agrochemistry, perfumery or the food industry. Mention may be made of the document WO 1998/02500, which describes compositions comprising at least one catechol derivative, an aromatic solvent and an alcohol. These compositions are used as polymerization inhibitors. These compositions remain liquid at temperatures ranging down to −50° C. and thus make it possible to avoid the use of thermostatically controlled industrial lines.

In view of this broad field of exploitation, it is necessary to produce these products at an industrial scale and to have available optimized manufacturing processes.

Conventionally, hydroquinone and catechol are produced by hydroxylation of phenol by hydrogen peroxide in the presence of an acid catalyst, strong protic acid (for example in FR 2 071 464) or else a solid catalyst having acid properties, such as, for example, the zeolite TS-1 (FR 2 489 816), a zeolite of MEL titanium silicalite type (EP 1 131 264), a titanozeolite of MFI type (EP 1 123 159) or also a zeolite MCM-22 (FR 2 856 681).

One of the challenges of these processes is to optimize in a general fashion the productivity of the reaction in order to be able to meet the demand for hydroquinone and for catechol. The optimized parameters might in particular be the yields of the reaction, the ratio of hydroquinone to catechol or the energy efficiency of the reaction.

In order to respond to this general problem of productivity, numerous documents report specific reaction conditions. For example, the nature of the solvent or of the solvents used for the reaction is described in the scientific publication by Thangaraj et al., Indian Journal of Chemistry, Vol. 33A, March 1994, pp. 255-258, and also in the patent application EP 3 048 091 and in the patent U.S. Pat. No. 5,426,244.

On conclusion of such a hydroxylation reaction, a mixture comprising hydroquinone and catechol, in variable proportions, and also various byproducts, such as resorcinol, pyrogallol, and the like, is generally obtained. To the knowledge of the inventors, the formation of undesirable byproducts derived from the solvent or from the solvents has never been studied, in the context of a reaction for the hydroxylation of phenol. In point of fact, the presence of these byproducts may have an influence on the effectiveness of the reaction itself and also on the subsequent purification processes.

BRIEF DESCRIPTION OF THE INVENTION

It is to the credit of the applicant company to have identified a novel hydroquinone and/or catechol composition containing certain byproducts, the nature and the contents of which are controlled.

Thus, a first subject matter of the present invention is a composition comprising at least one compound selected from hydroquinone and catechol, characterized in that it additionally comprises between 0.1 and 10 000 ppm of at least one compound selected from 2-(alkoxy)phenol, 4-(alkoxy)phenol, 2-(alkyl)phenol, 4-(alkyl)phenol, (alkyl) catechol, (alkyl)hydroquinone and alkoxybenzene.

Preferably, a subject matter of the present invention is a composition comprising at least one compound selected from hydroquinone and catechol, characterized in that it additionally comprises between 0.1 and 10 000 ppm of at least one compound selected from 2-(tert-butoxy)phenol, 4-(tert-butoxy)phenol, 2-(tert-butyl)phenol, 4-(tert-butyl) phenol, (tert-butyl)catechol, (tert-butyl)hydroquinone and tert-butoxybenzene.

According to another aspect, a subject matter of the present invention is a composition comprising at least one compound selected from hydroquinone and catechol, characterized in that it additionally comprises between 0.1 and 10 000 ppm of at least one compound selected from 2-(isopropoxy)phenol, 4-(isopropoxy)phenol, 2-isopropylphenol, 4-isopropylphenol, isopropylcatechol, isopropylhydroquinone and isopropylbenzene.

Another aspect of this invention relates to a process for the preparation of a composition comprising at least one compound selected from hydroquinone and catechol according to the invention, characterized in that it comprises a step (a) of reaction of phenol with hydrogen peroxide in the presence of a catalyst, in a solvent comprising an alcohol, or a mixture of alcohols, preferably selected from isopropanol, 2,2-dimethylpropanol and tert-butanol.

DETAILED DESCRIPTION

In the context of the present invention, and unless otherwise indicated, the expression "between . . . and . . . " includes the limits. Unless otherwise indicated, the percentages and ppm are percentages and ppm by weight.

In the context of the present invention, and unless otherwise indicated, the expression "alkyl" represents a linear or branched chain comprising from 1 to 6 carbon atoms.

In the context of the present invention, and unless otherwise indicated, the expression "alkoxy" represents an alkyl group bonded to an oxygen atom: R—O.

In the context of the present invention, and unless otherwise indicated, the term "ppm" means "parts per million". This unit represents a fraction by weight: 1 ppm=1 mg/kg.

A first aspect of the present invention is a composition comprising at least one compound selected from hydroquinone and catechol, characterized in that it additionally comprises between 0.1 and 10 000 ppm of at least one compound selected from 2-(alkoxy)phenol, 4-(alkoxy)phenol, 2-(alkyl)phenol, 4-(alkyl)phenol, (alkyl)catechol, (alkyl)hydroquinone and alkoxybenzene.

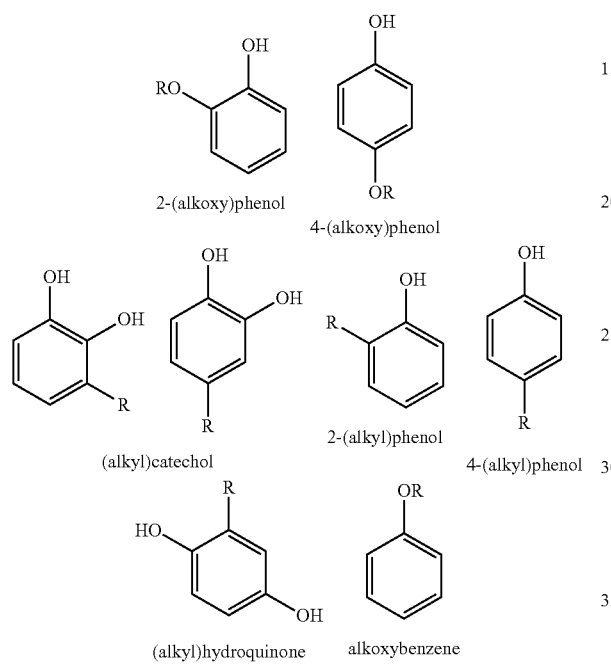

Preferably, the composition comprising at least one compound selected from hydroquinone and catechol is characterized in that it additionally comprises at least one compound selected from 2-(alkoxy)phenol, 4-(alkoxy)phenol, 2-(alkyl)phenol, 4-(alkyl)phenol, (alkyl)catechol and (alkyl)hydroquinone in an amount:
- of greater than or equal to 0.5 ppm, preferably an amount of greater than or equal to 1 ppm and more preferably still an amount of greater than or equal to 10 ppm; and/or
- of less than or equal to 500 ppm, preferably an amount of less than or equal to 300 ppm and more preferably still an amount of less than or equal to 100 ppm.

In addition, the composition according to the present invention may comprise an amount of greater than or equal to 1 ppm, preferably an amount of greater than or equal to 10 ppm and more preferably still an amount of greater than or equal to 100 ppm of alkoxybenzene. The composition according to the present invention may additionally an amount of less than or equal to 10 000 ppm, preferably an amount of less than or equal to 5000 ppm and more preferably still an amount of less than or equal to 1000 ppm of alkoxybenzene.

According to a specific aspect, the composition according to the present invention does not comprise an aromatic solvent.

In the context of the present invention, it is also possible for derivatives of dialkoxylated, dialkylated or alkylated and alkoxylated types to be formed during the reaction. Mention may be made, without limitation, of derivatives of the 2,3-dialkoxyphenol, 2,6-dialkoxyphenol, 2,3-dialkylphenol, 2,6-dialkylphenol, 2-alkoxy-6-alkylphenol or 2-alkoxy-3-alkylphenol type.

Advantageously, a subject matter of the present invention relates to a composition comprising at least one compound selected from hydroquinone and catechol, characterized in that it additionally comprises between 0.1 and 10 000 ppm of at least one compound selected from 2-(tert-butoxy)phenol, 4-(tert-butoxy)phenol, 2-(tert-butyl)phenol, 4-(tert-butyl)phenol, (tert-butyl)catechol, (tert-butyl)hydroquinone and tert-butoxybenzene.

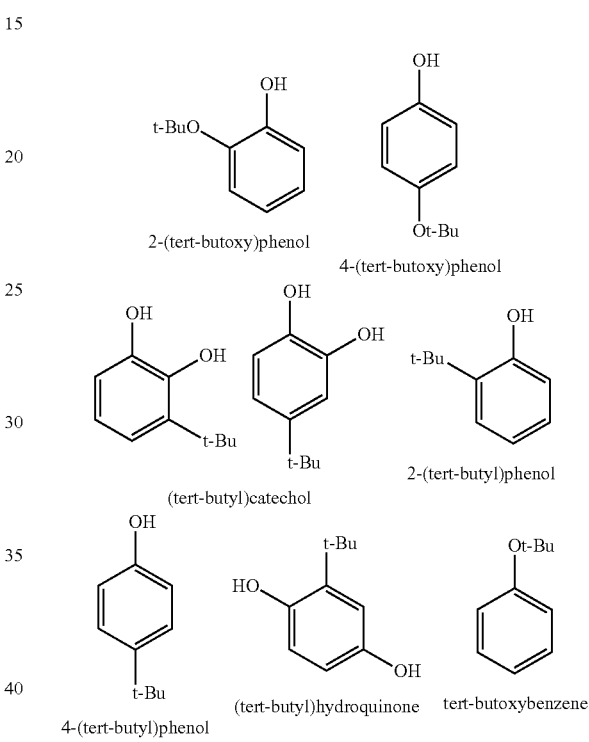

Preferably, the composition comprising at least one compound selected from hydroquinone and catechol is characterized in that it additionally comprises at least one compound selected from 2-(tert-butoxy)phenol, 4-(tert-butoxy)phenol, 2-(tert-butyl)phenol, 4-(tert-butyl)phenol, (tert-butyl)catechol and (tert-butyl)hydroquinone in an amount:
- of greater than or equal to 0.5 ppm, preferably an amount of greater than or equal to 1 ppm and more preferably still an amount of greater than or equal to 10 ppm; and/or
- of less than or equal to 500 ppm, preferably an amount of less than or equal to 300 ppm and more preferably still an amount of less than or equal to 100 ppm.

In addition, the composition according to the present invention may comprise an amount of greater than or equal to 1 ppm, preferably an amount of greater than or equal to 10 ppm and more preferably still an amount of greater than or equal to 100 ppm of tert-butoxybenzene. The composition according to the present invention may additionally an amount of less than or equal to 10 000 ppm, preferably an amount of less than or equal to 5000 ppm and more preferably still an amount of less than or equal to 1000 ppm of tert-butoxybenzene.

Advantageously, a subject matter of the present invention relates to a composition comprising at least one compound selected from hydroquinone and catechol, characterized in that it additionally comprises between 0.1 and 10 000 ppm of at least one compound selected from 2-(isopropoxy) phenol, 4-(isopropoxy)phenol, 2-isopropylphenol, 4-isopropylphenol, isopropylcatechol, isopropylhydroquinone and isopropylbenzene.

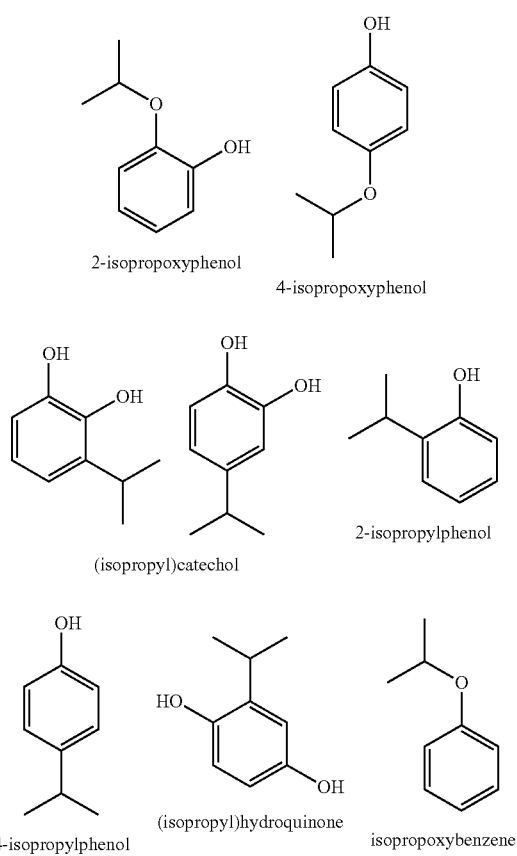

Preferably, the composition comprising at least one compound selected from hydroquinone and catechol is characterized in that it additionally comprises at least one compound selected from 2-(isopropoxy)phenol, 4-(isopropoxy)phenol, 2-isopropylphenol, 4-isopropylphenol, isopropylcatechol and isopropylhydroquinone in an amount:
  of greater than or equal to 0.5 ppm, preferably an amount of greater than or equal to 1 ppm and more preferably still an amount of greater than or equal to 10 ppm; and/or
  of less than or equal to 500 ppm, preferably an amount of less than or equal to 300 ppm and more preferably still an amount of less than or equal to 100 ppm.

In addition, the composition according to the present invention may comprise an amount of greater than or equal to 1 ppm, preferably an amount of greater than or equal to 10 ppm and more preferably still an amount of greater than or equal to 100 ppm of isopropylbenzene. The composition according to the present invention may additionally an amount of less than or equal to 10 000 ppm, preferably an amount of less than or equal to 5000 ppm and more preferably still an amount of less than or equal to 1000 ppm of isopropylbenzene.

One aspect of the present invention relates to a composition comprising:
  at least 80% of hydroquinone, preferably at least 90% of hydroquinone, more preferably at least 99% of hydroquinone, and
  an amount of greater than or equal to 0.1 ppm, preferably an amount of greater than or equal to 1 ppm and more preferably still an amount of greater than or equal to 10 ppm of at least one compound selected from 2-(alkoxy) phenol, 4-(alkoxy)phenol, (alkyl)catechol and (alkyl) hydroquinone.

Advantageously, the amount of at least one compound selected from 2-(alkoxy)phenol, 4-(alkoxy)phenol, (alkyl) catechol and (alkyl)hydroquinone may be less than or equal to 1000 ppm, preferably less than or equal to 500 ppm and more preferably still less than or equal to 100 ppm.

According to another aspect, the invention relates to a composition comprising:
  at least 80% of catechol, preferably at least 90% of catechol, more preferably at least 99% of catechol, and
  an amount of greater than or equal to 0.1 ppm, preferably an amount of greater than or equal to 1 ppm and more preferably still an amount of greater than or equal to 10 ppm of at least one compound selected from 2-(alkyl) phenol and 4-(alkyl)phenol.

Advantageously, the amount of at least one compound selected from 2-(alkyl)phenol and 4-(alkyl)phenol may be less than or equal to 1000 ppm, preferably less than or equal to 500 ppm and more preferably still or equal to 100 ppm.

Advantageously, the present invention relates to a composition comprising:
  at least 80% of hydroquinone, preferably at least 90% of hydroquinone, more preferably at least 99% of hydroquinone, and
  an amount of greater than or equal to 0.1 ppm, preferably an amount of greater than or equal to 1 ppm and more preferably still an amount of greater than or equal to 10 ppm of at least one compound selected from 2-(tert-butoxy)phenol, 4-(tert-butoxy)phenol, (tert-butyl)catechol and (tert-butyl)hydroquinone.

Advantageously, the amount of at least one compound selected from 2-(tert-butoxy)phenol, 4-(tert-butoxy)phenol, (tert-butyl)catechol and (tert-butyl)hydroquinone may be less than or equal to 1000 ppm, preferably less than or equal to 500 ppm and more preferably still less than or equal to 100 ppm.

According to another aspect, the invention relates to a composition comprising:
  at least 80% of catechol, preferably at least 90% of catechol, more preferably at least 99% of catechol, and
  an amount of greater than or equal to 0.1 ppm, preferably an amount of greater than or equal to 1 ppm and more preferably still an amount of greater than or equal to 10 ppm of at least one compound selected from 2-(tert-butyl)phenol and 4-(tert-butyl)phenol.

Advantageously, the amount of at least one compound selected from 2-(tert-butyl)phenol and 4-(tert-butyl)phenol may be less than or equal to 1000 ppm, preferably less than or equal to 500 ppm and more preferably still or equal to 100 ppm.

Advantageously, the present invention relates to a composition comprising:
  at least 80% of hydroquinone, preferably at least 90% of hydroquinone, more preferably at least 99% of hydroquinone, and
  an amount of greater than or equal to 0.1 ppm, preferably an amount of greater than or equal to 1 ppm and more preferably still an amount of greater than or equal to 10 ppm of at least one compound selected from 2-(isopropoxy)phenol, 4-(isopropoxy)phenol, isopropylcatechol and isopropylhydroquinone.

Advantageously, the amount of at least one compound selected from 2-(isopropoxy)phenol, 4-(isopropoxy)phenol, isopropylcatechol and isopropylhydroquinone may be less than or equal to 1000 ppm, preferably less than or equal to 500 ppm and more preferably still less than or equal to 100 ppm.

According to another aspect, the invention relates to a composition comprising:
 at least 80% of catechol, preferably at least 90% of catechol, more preferably at least 99% of catechol, and
 an amount of greater than or equal to 0.1 ppm, preferably an amount of greater than or equal to 1 ppm and more preferably still an amount of greater than or equal to 10 ppm of at least one compound selected from 2-isopropylphenol and 4-isopropylphenol.

Advantageously, the amount of at least one compound selected from 2-isopropylphenol and 4-isopropylphenol may be less than or equal to 1000 ppm, preferably less than or equal to 500 ppm and more preferably still or equal to 100 ppm.

The compositions which are a subject matter of the present invention are particularly advantageous as they respond to a need to control an industrial process. The presence and the content of the byproducts mentioned are compatible, on the one hand, with a process for the hydroxylation of phenol of high productivity offering a large operating window for the production of PC and HQ and, on the other hand, with the purification processes, which makes it possible to control the overall costs of the process.

Another aspect of the present invention relates to a process for the preparation of a composition comprising at least one compound selected from hydroquinone and catechol according to the invention, characterized in that it comprises a step (a) of reaction of phenol with hydrogen peroxide in the presence of a catalyst, in a solvent comprising an alcohol, or a mixture of alcohols, preferably selected from isopropanol, 2,2-dimethylpropanol and tert-butanol.

Step (a) corresponds to a hydroxylation of phenol. This process makes possible the synthesis of hydroquinone (HQ) and of catechol (PC). Advantageously, the process according to the invention makes it possible to control the PC/HQ ratio. The PC/HQ molar ratio is less than or equal to 1, preferably less than or equal to 0.7.

The hydrogen peroxide ($H_2O_2$) used in the present invention may be in solution in water. Any dilution of $H_2O_2$ in water may be used. An ordinary concentration of 30% in water may be used in the context of this process but an aqueous solution exhibiting a greater concentration in water may also be used, as is or in the form diluted with an inert solvent, which may be selected from alcohols, preferably methanol, ethanol, isopropanol, butanol or tert-butanol. The hydrogen peroxide may be added all at once. The hydrogen peroxide may also be added portionwise to the reaction over a given period of time.

According to the process of the present invention, the reaction is carried out in the presence of a catalyst, preferably a heterogeneous catalyst. The catalyst may be a titanium-comprising zeolite. These zeolites may exhibit a structure of the MFI family or of the MEL family. The catalyst may be a titanosilicalite. The composition of the titanosilicalite according to the present invention may be represented by the following structure: $(SiO_2)_x(TiO_2)_{(1-x)}$. The value of x/(1-x) may be between 5 and 1000, preferably between 10 and 500. The titanosilicalite may be prepared according to methods known to a person skilled in the art; mention may be made, for example, of the process of the document U.S. Pat. No. 4,410,501. The catalyst may preferably be a TS-1, TS-2, Ti-MWW or Ti-MCM68; more preferably, the catalyst is a TS-1.

The amount of catalyst used in the present invention is generally greater than or equal to 0.1% by weight, with respect to the phenol, preferably greater than or equal to 0.4% by weight. The amount of catalyst used in the present invention is generally less than or equal to 30% by weight, preferably less than or equal to 20% by weight.

In the process according to the invention, the solvent comprises an alcohol, or a mixture of alcohols; preferably, the alcohol is selected from isopropanol, 2,2-dimethylpropanol and tert-butanol. Said alcohol may be used alone or with a cosolvent. The cosolvent may advantageously be selected from water.

Advantageously, the ratio by weight of the alcohol used in the reaction to the cosolvent may be between 1:99 and 90:10, preferably between 3:97 and 80:20.

The amount of alcohol used represents between 1% and 90% by weight, preferably between 3% and 50% by weight, with respect to the total weight of liquid in the reaction.

The amount of water used may be the amount of water contributed by the aqueous hydrogen peroxide solution. The amount of cosolvent represents between 5% and 90% by weight, preferably between 8% and 90% by weight, more preferably between 8% and 85% by weight, with respect to the total weight of liquid in the reaction.

Preferably, in the process according to the invention, the solvent comprises tert-butanol. The tert-butanol may be used alone or with a cosolvent. The cosolvent may advantageously be selected from water, acetone, acetonitrile, 1,4-dioxane or an alcohol of formula R'—OH, or their mixtures, where R' represents a linear or branched alkyl chain comprising from 1 to 6 carbon atoms; preferably, the alcohol is selected from methanol, ethanol, isopropanol, n-propanol and n-butanol. Advantageously, the ratio by weight of the tert-butanol used in the reaction to the cosolvent may be between 1:99 and 90:10, preferably between 3:97 and 80:20.

The amount of tert-butanol used represents between 1% and 90% by weight, preferably between 3% and 50% by weight, with respect to the total weight of liquid in the reaction.

The amount of water used may be the amount of water contributed by the aqueous hydrogen peroxide solution. The amount of cosolvent represents between 5% and 90% by weight, preferably between 8% and 90% by weight, more preferably between 8% and 85% by weight, with respect to the total weight of liquid in the reaction.

The temperature of the reaction may be greater than or equal to 30° C., preferably greater than or equal to 40° C. The temperature of the reaction may be less than or equal to 130° C., preferably less than or equal to 100° C.

This process may be carried out continuously, semicontinuously or batchwise.

On conclusion of step (a), it is possible to advantageously obtain the composition according to the invention comprising at least one compound selected from hydroquinone and catechol, characterized in that it additionally comprises between 0.1 and 10 000 ppm of at least one compound selected from 2-(alkoxy)phenol, 4-(alkoxy)phenol, 2-(alkyl)phenol, 4-(alkyl)phenol, (alkyl)catechol, (alkyl)hydroquinone and alkoxybenzene.

Preferably, on conclusion of step (a), it is possible to advantageously obtain the composition according to the invention comprising at least one compound selected from hydroquinone and catechol, characterized in that it additionally comprises between 0.1 and 10 000 ppm of at least one compound selected from 2-(tert-butoxy)phenol, 4-(tert-butoxy)phenol, 2-(tert-butyl)phenol, 4-(tert-butyl)phenol, (tert-butyl)catechol, (tert-butyl)hydroquinone and tert-butoxybenzene.

Preferably, on conclusion of step (a), it is possible to advantageously obtain the composition according to the invention comprising at least one compound selected from hydroquinone and catechol, characterized in that it additionally comprises between 0.1 and 10 000 ppm of at least one compound selected from 2-(isopropoxy)phenol, 4-(isopropoxy)phenol, 2-isopropylphenol, 4-isopropylphenol, isopropylcatechol, isopropylhydroquinone and isopropylbenzene.

According to one embodiment of the present invention, the process described above may additionally comprise a step (b) of purification of the composition obtained in step (a). The choice of the purification method is not particularly restricted. The purification method used may in particular be selected from liquid/liquid extraction, distillation, crystallization or a combination of these methods.

According to another embodiment of the present invention, the process according to the invention may additionally comprise a step (c) of separation of the hydroquinone and catechol.

Thus, on conclusion of step (c), it is possible to obtain:
 on the one hand, a composition comprising at least 80% of hydroquinone and between 0.1 and 1000 ppm of at least one compound selected from 2-(alkoxy)phenol, 4-(alkoxy)phenol, (alkyl)catechol and (alkyl)hydroquinone,
 and, on the other hand, a composition comprising at least 80% of catechol and between 0.1 and 1000 ppm of at least one compound selected from 2-(alkyl)phenol and 4-(alkyl)phenol.

Preferably, on conclusion of step (c), it is possible to obtain:
 on the one hand, a composition comprising at least 80% of hydroquinone and between 0.1 and 1000 ppm of at least one compound selected from 2-(tert-butoxy)phenol, 4-(tert-butoxy)phenol, (tert-butyl)catechol and (tert-butyl)hydroquinone,
 and, on the other hand, a composition comprising at least 80% of catechol and between 0.1 and 1000 ppm of at least one compound selected from 2-(tert-butyl)phenol and 4-(tert-butyl)phenol.

Preferably, on conclusion of step (c), it is possible to obtain:
 on the one hand, a composition comprising at least 80% of hydroquinone and between 0.1 and 1000 ppm of at least one compound selected from 2-(isopropoxy)phenol, 4-(isopropoxy)phenol, isopropylcatechol and isopropylhydroquinone,
 and, on the other hand, a composition comprising at least 80% of catechol and between 0.1 and 1000 ppm of at least one compound selected from 2-isopropylphenol and 4-isopropylphenol.

Optionally, the process according to the present invention may comprise at least one step (d) of shaping the products obtained in step (c). The choice of the method of shaping the products obtained on conclusion of step (c) is not restricted. The products obtained according to the process of the invention may thus be crystalline or in amorphous powder form. The products obtained according to the process of the invention may be shaped as amorphous or crystalline flakes, beads, balls or pellets.

The invention claimed is:

1. A composition, comprising:
 at least one compound selected from the group consisting of hydroquinone and catechol, and between 0.1 and 10,000 ppm of at least one compound selected from the group consisting of
 2-(alkoxy)phenols, 4-(alkoxy)phenols, 2-(alkyl)phenols, 4-(alkyl)phenols, (alkyl)catechols, (alkyl)hydroquinones, and alkoxybenzenes, wherein the alkoxy is selected from the group consisting of tert-butoxy 2,2-dimethylpropoxy and isopropoxy and the alkyl is selected from the groups consisting of tert-butyl, 2,2-dimethylpropyl and isopropyl.

2. The composition as claimed in claim 1, wherein the composition comprises at least 80% of hydroquinone and between 0.1 and 1000 ppm of at least one compound selected from the group consisting of 2-(alkoxy)phenols, 4-(alkoxy)phenols, (alkyl)catechols, and (alkyl)hydroquinones.

3. The composition as claimed in claim 1, wherein the composition comprises at least 80% of catechol and between 0.1 and 1000 ppm of at least one compound selected from the group consisting of 2-(alkyl)phenols and 4-(alkyl)phenols.

4. The composition as claimed in claim 1, wherein the at least one compound selected from the group consisting of 2-(alkoxy)phenols, 4-(alkoxy)phenols, 2-(alkyl)phenols, 4-(alkyl)phenols, (alkyl)catechols, (alkyl)hydroquinones, and alkoxybenzenes comprises at least one of 2-(tert-butoxy)phenol, 4-(tert-butoxy)phenol, 2-(tert-butyl)phenol, 4-(tert-butyl)phenol, (tert-butyl)catechol, (tert-butyl)hydroquinone and tert-butoxybenzene.

5. The composition as claimed in claim 1, wherein the at least one compound selected from the group consisting of 2-(alkoxy)phenols, 4-(alkoxy)phenols, 2-(alkyl)phenols, 4-(alkyl)phenols, (alkyl)catechols, (alkyl)hydroquinones, and alkoxybenzenes comprises at least one of 2-(isopropoxy)phenol, 4-(isopropoxy)phenol, 2-isopropylphenol, 4-isopropylphenol, isopropylcatechol, isopropylhydroquinone and isopropylbenzene.

6. A process for the preparation of a composition according to claim 1, comprising:
 (a) reacting phenol with hydrogen peroxide in the presence of a catalyst, in a solvent consisting of an alcohol, or a mixture of alcohols or water and an alcohol or a mixture of alcohols, wherein the alcohol or mixture of alcohols is selected from the group consisting of isopropanol, 2,2-dimethylpropanol, tert-butanol, and mixtures thereof.

7. The process as claimed in claim 6, further comprising:
 (b) purifying the composition obtained in step (a).

8. The process as claimed in claim 7, wherein the composition comprises hydroquinone and catechol, further comprising:
 (a) separating hydroquinone and catechol, and, optionally:
 (b) shaping the hydroquinone and catechol obtained in step (c).

9. The process as claimed in claim 6, wherein the catalyst is a heterogeneous catalyst.

10. The process of claim 8, wherein the process comprises step (d) and the products obtained in step (d) are in the form of a crystalline or amorphous powder.

11. The process of claim 9, wherein the heterogeneous catalyst is a titanium-comprising zeolite.

12. The process of claim 9, wherein the heterogeneous catalyst is a TS-1, TS-2, Ti-MWW, or Ti-MCM68 zeolite.

13. The process of claim 9, wherein the heterogeneous catalyst is a TS-1 zeolite.

* * * * *